(12) United States Patent
Beglova

(10) Patent No.: US 8,993,518 B2
(45) Date of Patent: Mar. 31, 2015

(54) COMPOSITIONS AND METHODS FOR TREATING ANTIPHOSPHOLIPID SYNDROME

(75) Inventor: Natalia Beglova, Holliston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 13/881,284

(22) PCT Filed: Oct. 31, 2011

(86) PCT No.: PCT/US2011/058522
§ 371 (c)(1),
(2), (4) Date: Apr. 24, 2013

(87) PCT Pub. No.: WO2012/061268
PCT Pub. Date: May 10, 2012

(65) Prior Publication Data
US 2013/0252887 A1    Sep. 26, 2013

Related U.S. Application Data

(60) Provisional application No. 61/410,690, filed on Nov. 5, 2010.

(51) Int. Cl.
*C07K 14/705* (2006.01)
*A61K 38/17* (2006.01)
*C07K 14/775* (2006.01)

(52) U.S. Cl.
CPC .............. *C07K 14/705* (2013.01); *A61K 38/177* (2013.01); *C07K 14/775* (2013.01); *C07K 2319/21* (2013.01); *C07K 2319/50* (2013.01)
USPC .......................................... 514/7.4; 530/350

(58) Field of Classification Search
CPC .... C07K 14/705; C07K 14/775; C07K 19/00; C07K 2319/21; C07K 2319/50; A61K 38/177; A61K 38/00; C12N 15/62
See application file for complete search history.

(56) References Cited

U.S. PATENT DOCUMENTS

2003/0138419 A1    7/2003    Radic et al.
2010/0047163 A1    2/2010    Forte et al.

OTHER PUBLICATIONS http://www.nhlbi.nih.gov/health/health-topics/topics/stroke/treatment.html (Feb. 2011).*
http://www.webmd.com/children/intellectual-disability-mental-retardation (accessed Feb. 3, 2014).*
Beglov et al., "Structural insights into recognition of β2-glycoprotein I by the lipoprotein receptors," *Proteins* 77:940-949 (2009).
International Preliminary Report on Patentability and written opinion for International Application No. PCT/US2011/58522, issued May 7, 2013 (6 pages).
Matthews, "Uniprot Accession B1AXJ6," <http://www.uniprot.org/uniprot/B1AXJ6.txt?> retrieved on Feb. 27, 2012 (2 pages).
Yasuda, "Pathogenic roles of anti-$β_2$-GPI antibody in patients with antiphospholipid syndrome," *Jpn J Clin Immunol.* 27:373-378 (2004).
Lee et al., "Mode of interaction between beta2GPI and lipoprotein receptors suggests mutually exclusive binding of beta2GPI to the receptors and anionic phospholipids," *Structure* 18(3):366-76 (2010).

* cited by examiner

*Primary Examiner* — James H Alstrum Acevedo
*Assistant Examiner* — Tara Martinez
(74) *Attorney, Agent, or Firm* — Clark & Elbing LLP; Kristina Bieker-Brady; Todd Armstrong

(57) ABSTRACT

The invention features compositions and methods of using a dimeric inhibitor, e.g., A1-A1, to selectively target β2GPI in β2GPI/antibody complexes. The compositions can be administered to subjects (e.g., a mammal, such as a human) having or likely to develop APS, or one or more symptoms of APS, in order to treat or inhibit the disease or treat or reduce its symptoms. The inhibitors of the invention include two ligand-binding A1 modules, e.g., from ApoER2, connected by a flexible linker.

26 Claims, 10 Drawing Sheets

COMPOSITIONS AND METHODS FOR TREATING ANTIPHOSPHOLIPID SYNDROME

CROSS-REFERENCE TO RELATED APPLICATIONS

This application is the U.S. National Stage filing under 35 U.S.C. §371 of International Application No. PCT/US2011/058522, filed on Oct. 31, 2011, which claims benefit of U.S. provisional application No. 61/410,690, filed Nov. 5, 2010, the contents of which are incorporated herein by reference.

FIELD OF THE INVENTION

The invention provides methods for the treatment of antiphospholipid syndrome (APS), in particular clots (thrombosis) and pregnancy-related complications, such as miscarriage, stillbirth, preterm delivery, and preeclampsia, associated therewith in patients (e.g., human patients) having APS.

BACKGROUND OF THE INVENTION

Beta2-glycoprotein I (β2GPI) is the major target for autoimmune antibodies associated with antiphospholipid syndrome (APS), an autoimmune disease characterized clinically by clots (thrombosis) in both arteries and veins, as well as pregnancy-related complications such as miscarriage, stillbirth, preterm delivery, and preeclampsia (Atsumi et al., Autoimmunity 38:377-381, 2005; Galli et al., Lancet 335: 1544-1547, 1990; McNeil et al., Proc Nat Acad Sci USA 87:4120-4124, 1990; Miyakis et al., J Thromb Haemost 4:295-306, 2006). Presently, APS patients with thrombotic complications who have high titers of antibodies are treated chronically with anticoagulants (George et al., Prog Cardiovasc Dis 52:115-125, 2009; Lim et al., JAMA 295:1050-1057, 2006; McKnall-Knapp, Curr Rheumatol Rep 10:62-66, 2008). However, even continuous anticoagulation may not prevent recurrent thrombosis (George et al., Prog Cardiovasc Dis 52:115-125, 2009), emphasizing the need for a more effective antithrombotic therapy based on the thrombogenic mechanisms specific to APS.

β2GPI consists of five domains connected by short three- to four-residue linkers (Bouma et al., Embo J 18:5166-5174, 1999; Schwarzenbacher et al., Embo J 18:5166-5174, 1999). Flexible linkers between domains permit β2GPI to adopt different overall shapes such as a fishhook-like shape seen in the crystal structure (Bouma et al., Embo J 18:5166-5174, 1999; Schwarzenbacher et al., Embo J 18:5166-5174, 1999), an S-shape observed by small angle x-ray scattering for β2GPI in solution (Hammel et al., J Mol Biol 321:85-97, 2002) and a circular shape detected by electron microscopy (Agar et al., Blood, 2010). The circular shape in which domain I is adjacent to domain V is the predominant conformation of β2GPI in normal human plasma (Agar et al., Blood, 2010). Circular β2GPI can be converted to an extended form by altering pH and salt concentrations, binding to a high-affinity antibody directed to domain I or by the binding to cardiolipin (Agar et al., Blood, 2010). β2GPI, which is abundant in plasma (about 170 µg/ml) (Lin et al. Lupus 15:87-93, 2006), acquires its prothrombotic properties only in the presence of anti-β2GPI antibodies. Antibodies of the IgG isotype have the highest correlation with the clinical manifestations of APS compared to other identified antibodies (Laat et al., Blood 104:3598-3602, 2004; Guerin et al., Autoimmunity 31:109-116, 1999). Although anti-β2GPI antibodies in APS patients are highly heterogeneous in respect to their affinity for β2GPI and the location of their binding epitopes, autoantibodies against domain I are the most common and better correlate with thrombosis (Laat et al., J Thromb Haemost, 2009; Ioannou et al., J Thromb Haemost 7:833-842, 2009). The presence of anti-β2GPI antibodies causes cellular activation both in vitro and in vivo (Cugno et al., J Autoimmun 34:105-110, 2010; Koike et al., J Autoimmun 28:129-133, 2007; Pierangeli et al., Thromb Res 114:467-476, 2004). Toll-like receptors, annexin A2, ApoER2, GPIb and anionic phospholipids exposed on cellular surfaces are suggested to be pathologically important in APS (Koike et al., J Autoimmun 28:129-133, 2007; Pierangeli et al., Thromb Res 114:467-476, 2004; Lutters et al. J Biol Chem 278:33831-33838, 2003; Pennings et al., J Thromb Haemost 5:369-377, 2007; Shi et al. Arthritis Rheum 54:2558-2567, 2006; Cockrell et al., Lupus 17:943-951, 2008; Raschi et al., Lupus 17:937-942, 2008; Urbanus et al., J Thromb Haemost, 2008; Pierangeli et al., Ann Rheum Dis 66:1327-1333, 2007; Romay-Penabad et al., Blood 114:3074-3083, 2009; Urbanus et al., Blood Rev 22:93-105, 2008; Rand et al., Lupus 19:460-469, 2010). The binding sites for anionic phospholipids (Hunt et al., J Immunol 152:653-659, 1994; Mehdi et al., Eur J Biochem 267: 1770-1776, 2000; Sanghera et al., Hum Mol Genet 6:311-316, 1997; Sheng et al., J Immunol 157:3744-3751, 1996), lipoprotein receptors (Lummel et al., J Biol Chem 280:36729-36736, 2005), and GPIb (Pennings et al., J Thromb Haemost 5:369-377, 2007) are in domain V of β2GPI (β2GPI-DV).

At present, the standard of care for APS is treatment with aspirin to inhibit platelet activation and/or warfarin as an anticoagulant. The goal of the prophylactic treatment is to manage the patient's clotting profiles (e.g., the patient's prothrombin time (PT)), as determined by, e.g., the prothrombin ratio (PR) or international normalised ratio (INR). Treatment is usually given only to patients that have experienced thrombotic symptoms. During pregnancy, low molecular weight heparin and low-dose aspirin are used instead of warfarin because of warfarin's teratogenicity. APS continues to be a health issue, especially for women, who constitute 75-90% of those affected by APS. There is a need for improved therapies for the treatment of APS in patients.

SUMMARY OF THE INVENTION

The invention features compositions and methods for the treatment or prevention of APS in a patient in need thereof (e.g., a mammalian patient, such as a human). In particular the invention features compositions and methods for treating clots (thrombosis) in patients with APS. The invention also features compositions and methods for treating pregnancy-related complications, such as miscarriage, stillbirth, preterm delivery, and preeclampsia in female patients having APS.

A first aspect of the invention features a composition containing an inhibitor capable of specifically binding to at least one β2GPI monomer (e.g., at least a first and second β2GPI monomer) in a dimeric β2GPI/antibody complex, or an analog or derivative thereof, for use in treating antiphospholipid syndrome, or one or more symptoms thereof, in a subject in need thereof. In an embodiment, the inhibitor is a first low density lipoprotein (LDL) receptor-type A (LA) module capable of binding to a first β2GPI monomer joined by a linker to a second LA module capable of binding to a second β2GPI monomer. In another embodiment, the inhibitor contains homologous or heterologous LA modules. In yet other embodiments, the modules of the inhibitor include an A1 domain (e.g., an A1 domain having an amino acid sequence having 85% or more (e.g., 90%, 95%, 97%, 99%, or 100%) sequence identity to any one of SEQ ID NOs: 2, 3, 14, and 15).

In still other embodiments, the inhibitor contains a first A1 domain having an amino acid sequence with 85% or more (e.g., 90%, 95%, 97%, 99%, or 100%) sequence identity to SEQ ID NO: 2 or 14, and a second A1 domain having an amino acid sequence with 85% or more (e.g., 90%, 95%, 97%, 99%, or 100%) sequence identity to SEQ ID NO: 3 or 15. In other embodiments, the linker has an amino acid sequence with 85% or more (e.g., 90%, 95%, 97%, 99%, or 100%) sequence identity to any one of SEQ ID NOs: 4-12 (e.g., the linker has the amino acid sequence of SEQ ID NO: 4). In other embodiments, the inhibitor has an amino acid sequence having 85% or more (e.g., 90%, 95%, 97%, 99%, or 100%) sequence identity to SEQ ID NO: 1 or SEQ ID NO: 13. In other embodiments, the composition is formulated for administration 1 to 10 times (e.g., 1, 2, 3, 4, 5, 6, 7, 8, 9, or 10 times) per day, week, or month; and the composition has a dosage of the inhibitor of 0.01 to 2000 mg/kg.

A second aspect of the invention features a method of treating antiphospholipid syndrome, or one or more symptoms thereof, in a subject (e.g., a mammal, such as a human) in need thereof by administering a composition of the first aspect of the invention to said subject. In other embodiments, administration of the composition of the first aspect of the invention (e.g., a dimeric inhibitor having an amino acid sequence with 85% or more (e.g., 90%, 95%, 97%, 99%, or 100%) sequence identity to SEQ ID NO: 1 or SEQ ID NO: 13) to, e.g., a patient in need thereof (e.g., a human patient) treats or reverses APS or one or more symptoms of APS, such as blood clots (e.g., arterial or venous clots (e.g., in any organ system), such as deep vein thrombosis of the lower extremities (e.g., blood clot of the deep veins of the legs), stroke, thrombocytopenia (low platelet count), heart valve disease, livedo reticularis (a skin condition), headaches, migraines, oscillopsia, and pregnancy-related complications (e.g., miscarriage, pre-eclampsia, placental infarctions, early deliveries, stillbirth, and mental and/or development retardation in a newborn).

By "specifically bind" is meant the preferential association of a binding agent (e.g., an inhibitor of the invention, such as a low density lipoprotein (LDL) receptor-type A (LA) module capable of binding to at least one β2GPI monomer, or an antibody, antibody fragment, receptor, ligand, or small molecule portion capable of binding to at least one β2GPI monomer) to a target molecule (e.g., at least one β2GPI monomer) or to a cell or tissue bearing the target molecule and not to non-target molecules or cells or tissues lacking the target molecule. It is recognized that a certain degree of non-specific interaction may occur between a binding agent and a non-target molecule (present alone or in combination with a cell or tissue). Nevertheless, specific binding may be distinguished as mediated through specific recognition of the target molecule. Specific binding results in a stronger association between the binding agent (e.g., a LA module, antibody, antibody fragment, receptor, ligand, or small molecule capable of binding to at least one β2GPI monomer) and the target molecule (e.g., at least one β2GPI monomer or cells bearing the target molecule) than between the binding agent and a non-target molecule or cells lacking the target molecule. Specific binding typically results in greater than 2-fold, preferably greater than 5-fold, more preferably greater than 10-fold and most preferably greater than 100-fold increase in the amount of bound binding agent (per unit time) to e.g., a target molecule or a cell or tissue bearing the target molecule, as compared to the binding of the binding agent to a non-target molecule or a cell or tissue lacking that target molecule. Binding agents bind to the target molecule with a dissociation constant of e.g., less than $10^{-6}$M, more preferably less than $10^{-7}$M, $10^{-8}$M, $10^{-9}$M, $10^{-10}$M, $10^{-11}$M, or $10^{-12}$M, and most preferably less than $10^{-13}$M, $10^{-14}$M, or $10^{-15}$M. Specific binding to a target molecule under such conditions requires a binding agent that is selected for its specificity for that particular target molecule. A variety of assay formats are appropriate for selecting binding agents (e.g., a LA module, antibody, antibody fragment, receptor, ligand, or small molecule capable of binding to at least one β2GPI monomer) capable of specifically binding to a particular target molecule (e.g., at least one β2GPI monomer). For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

The term "substantial identity" or "substantially identical," when used in the context of comparing a polynucleotide or polypeptide sequence to a reference sequence, means that the polynucleotide or polypeptide sequence is the same as the reference sequence or has a specified percentage of nucleotides or amino acid residues that are the same at the corresponding locations within the reference sequence when the two sequences are optimally aligned. For instance, an amino acid sequence that is "substantially identical" to a reference sequence has at least about 60% identity, preferably 65%, 70%, 75%, 80%, 85%, 90%, 91%, 92%, 93%, 94%, 95%, 96%, 97%, 98%, 99%, or higher percentage identity (up to 100%) to the reference sequence (e.g., the HSA amino acid sequence as set forth in SEQ ID NO:1, or a fragment thereof), when compared and aligned for maximum correspondence over the full length of the reference sequence as measured using a BLAST or BLAST 2.0 sequence comparison algorithms with default parameters, or by manual alignment and visual inspection (see, e.g., NCBI web site).

A "target molecule" or "target cell" is meant a molecule (e.g., a β2GPI monomer or portion thereof) or cell to which a binding agent (e.g., a LA module, antibody, antibody fragment, receptor, ligand, or small molecule capable of binding to at least one β2GPI monomer or portion thereof) can specifically bind. A target molecule can be present in a secreted form (i.e., separated from a cell surface), on the exterior of a target cell (e.g., as a cell-surface protein), or in the interior of a target cell.

By "treating" is meant the reduction (e.g., by at least 10%, 15%, 20%, 25%, 30%, 35%, 40%, 45%, 50%, 60%, 70%, 80%, 90%, 95%, 99%, or even 100%) in the progression or severity of a disease or disorder (e.g., APS), or in the progression, severity, or frequency of one or more symptoms of the disease or disorder in a patient (e.g., a human patient).

BRIEF DESCRIPTION OF THE DRAWINGS

FIGS. 1A-1D are HPLC chromatograms of products formed by oxidative refolding of A1 (1A and 10) and A1-A1 (1B and 10). The proteins were dialyzed in redox buffer in the presence of calcium (FIGS. 1A and 1B) or EDTA (FIGS. 10 and 1D) and eluted starting with a linear gradient of 0.1% per minute of acetonitrile containing 0.1% TFA starting at 15 minutes from 21% of acetonitrile/TFA (for A1) or 26% of acetonitrile/TFA (for A1-A1).

FIGS. 2A and 2B are graphs showing the binding (FIG. 2A) and inhibition of the binding (FIG. 2B) of β2GPI in normal human serum to cardiolipin. FIG. 2A: The binding of β2GPI in serum to cardiolipin-coated surface in the absence (triangles) and in the presence (circles) of anti-β2GPI antibodies. FIG. 2B: Inhibition of the binding of γ2GPI in human serum to cardiolipin in the presence of anti-β2GPI antibodies by the dimeric inhibitor A1-A1 (circles; SEQ ID NO: 1) and monomeric inhibitor A1 (triangles; amino acids 12-47 of mature murine ApoER2, which corresponds to amino acids 2-37 of SEQ ID NO:1). Fit to one-site binding and inhibition models was performed on the raw data. To facilitate comparison, the measured $OD_{405}$ values and the binding curves were normalized to the maximum binding obtained from the fit.

FIG. 4A shows the binding of β2GPI purified from human plasma to cardiolipin in the absence (triangles) and in the presence (circles) of anti-β2GPI antibodies. FIG. 4B shows inhibition of the binding of purified β2GPI to cardiolipin in the presence of anti-γ2GPI antibodies by the dimeric inhibitor A1-A1 (circles; SEQ ID NO: 1) and monomeric inhibitor A1 (triangles; amino acids 12-47 of mature murine ApoER2, which corresponds to amino acids 2-37 of SEQ ID NO:1). Fit to one-site binding and inhibition models was performed on the raw data. To facilitate comparison, the measured $OD_{405}$ values and the binding curves were normalized to the maximum binding obtained from the fit. FIG. 4C shows a comparison of the measured with expected binding of β2GPI to cardiolipin calculated based on the fit of the inhibition curves. Purified β2GPI bound to cardiolipin in the presence of anti-β2GPI antibody without inhibitor (gray bar), with A1-A1 (black bars), and with A1 (white bars). The $OD_{405}$ values were normalized to $OD_{405}$ measured in the absence of inhibitor. The values of measured relative binding +/−SD are indicated above bar. The values of expected relative binding were calculated from the fit of the titration data and are given in parenthesis.

FIG. 6 was generated with the program PYMOL (DeLano, The PyMOL Molecular Graphics System. In. Palo Alto, Calif., USA: DeLano Scientific, 2002).

FIG. 7A shows the binding of β2GPI-DV to cardiolipin in the absence (triangles) and in the presence (circles) of the dimerization antibodies. FIG. 7B shows inhibition of the binding of β2GPI-DV to cardiolipin in the presence of dimerization antibodies by the dimeric inhibitor A1-A1 (circles; SEQ ID NO: 1) and monomeric inhibitor A1 (triangles; amino acids 12-47 of mature murine ApoER2, which corresponds to amino acids 2-37 of SEQ ID NO:1). Fit to one-site binding and inhibition models was performed on the raw data. To facilitate comparison, the measured $OD_{405}$ values and the binding curves were normalized to the maximum binding obtained from the fit.

FIGS. 9A-9F are graphs showing stability of the A1-A1 inhibitor (SEQ ID NO: 1) in human serum at 37° C. HPLC chromatograms of A1-A1 incubated in human serum for the amount of time indicated on each panel (FIG. 9A—3 hours; FIG. 9B—1 day; FIG. 9C—2 days; FIG. 9D—6 days; FIG. 9E—9 days; and FIG. 9F—15 days). Elution of the A1-A1 inhibitor was monitored with a linear gradient of 0.1% per minute of acetonitrile with 0.1% TFA. The gradient started at 15 minutes from about 26% of acetonitrile/TFA.

FIG. 10 is a model showing complex formation between β2GPI, inhibitor, and anti-β2GPI antibody. The binding of A1-A1, but not monomeric A1, forms stable β2GPI/anti-β2GPI/A1-A1 complex regardless of localization of the epitope for anti-β2GPI antibody and whether circular or extended β2GPI is dimerized by antibody. β2GPI (blue), A1 or A1-A1 inhibitor (red) and anti-β2GPI antibody (green).

DETAILED DESCRIPTION OF THE INVENTION

Figure 1:
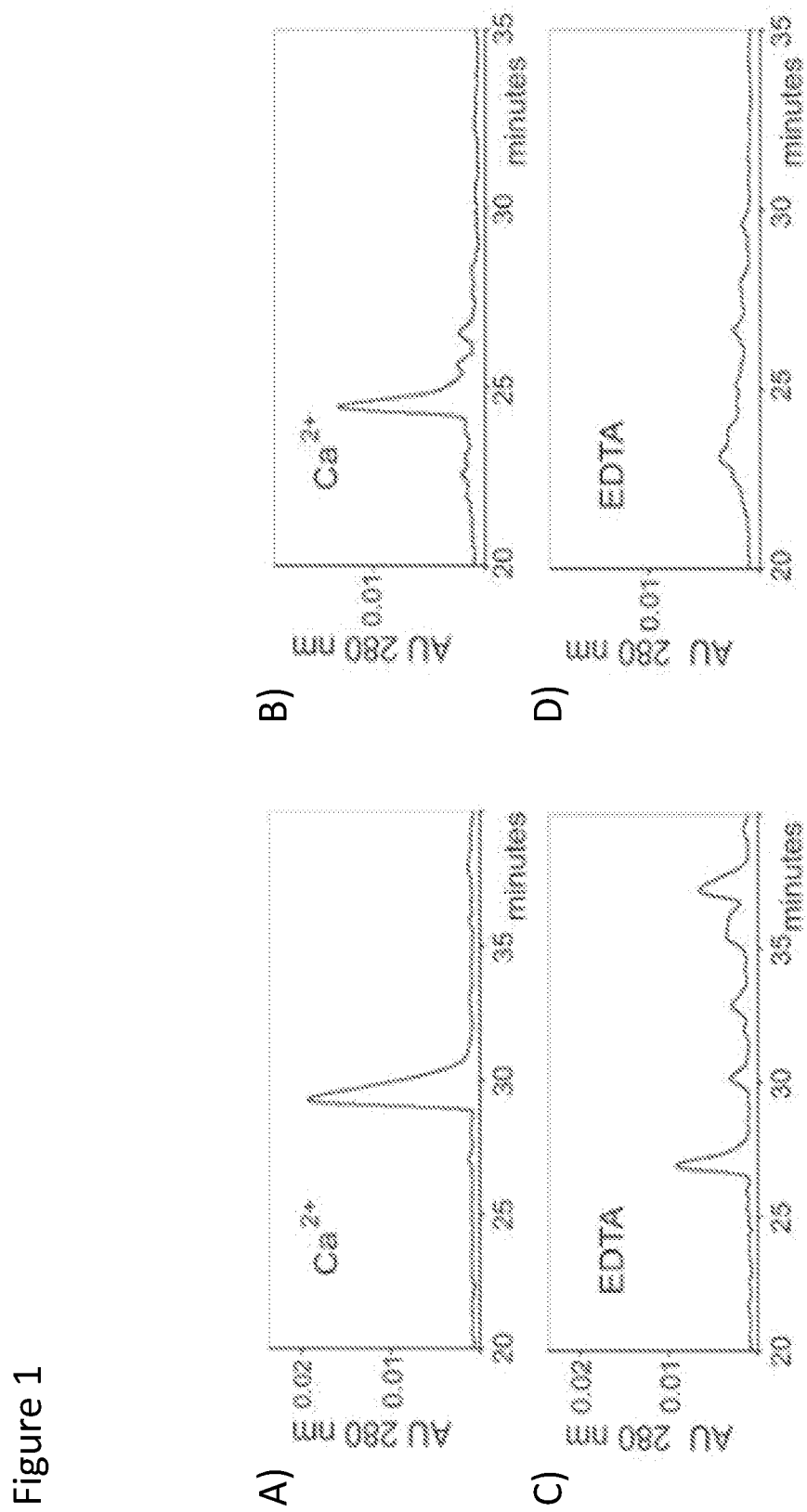

The present invention features a new approach for treating or preventing APS, or one or more symptoms of APS (e.g., anti-β2GPI-dependent thrombosis), that involves preventing the β2GPI/antibody complexes from binding to receptors. The invention features an inhibitor that a) targets β2GPI and b) binds tightly to β2GPI/antibody complexes expressing the dimeric β2GPI but binds weakly to β2GPI monomers. These requirements have the following rationale: First, complete β2GPI deficiency in humans, although rare, does not lead to apparent health problems (Bancsi et al., *Thromb Haemost* 67:649-653, 1992; Takeuchi et al., *Blood* 96:1594-1595, 2000; Yasuda et al., *Atherosclerosis* 152:337-346, 2000). Therefore the inhibitor that targets β2GPI will not disrupt normal biological processes. Second, β2GPI/anti-β2GPI antibody complexes expressing dimeric β2GPI but not monomeric β2GPI are pathologically important (Urbanus et al., *Blood Rev* 22:93-105, 2008; Lummel et al., *J Biol Chem* 280:36729-36736, 2005), therefore the inhibitor should bind preferentially to β2GPI/anti-β2GPI complex compared to β2GPI monomers. In contrast to β2GPI monomers, which are abundant in plasma, β2GPI/anti-β2GPI complexes are present at extremely low concentration.

The present invention features compositions and methods for inhibiting or reducing the binding of β2GPI/anti-β2GPI antibody complexes to ApoER2 and to anionic phospholipids. ApoER2, like other members of the family of lipoprotein receptors, binds β2GPI via structurally homologous LDL receptor-type A (LA) modules (Herz, *Annu Rev Biochem* 71:405-434, 2002; Jeon, *Annu Rev Biochem* 74:535-562, 2005; Pennings et al., *J Thromb Haemost* 4:1680-1690, 2006; Pennings et al., *J Thromb Haemost* 5:1538-1544, 2007). Different LA modules bind to the same site on β2GPI and β2GPI cannot simultaneously bind an LA module and a cardiolipin-coated surface (Lee et al., *Structure* 18:366-376, 2010). Therefore, an LA module bound to β2GPI has dual action it inhibits both the binding of β2GPI to lipoprotein receptors and to anionic phospholipids.

The invention features dimeric inhibitors that are prepared by connecting two ligand-binding LA modules from ApoER2 with a flexible linker (a single LA module is referred to as "A1," while the dimeric LA modules are referred to as "A1-A1"). We compared a monomeric A1 with A1-A1 on interfering with the binding of β2GPI/anti-β2GPI antibody complexes to anionic phospholipids. We tested the inhibition of β2GPI present in human serum, β2GPI purified from human plasma, and domain V of β2GPI. β2GPI in serum is the circular form of β2GPI (Agar et al., *Blood,* 2010) and the individual domain V represents β2GPI in the extended conformation. We demonstrated that when β2GPI/antibody complexes are formed, A1-A1 is more effective than A1 in inhibition of β2GPI binding to cardiolipin, regardless of the source of β2GPI. Similarly, A1-A1 strongly inhibits the binding of dimerized domain V of β2GPI to cardiolipin compared to the monomeric A1 inhibitor. Moreover, A1-A1 preferentially binds β2GPI/anti-β2GPI antibody complexes and binds only weakly to monomeric β2GPI. The present inhibitor A1-A1 can be used to effectively treat or reduce one or more symptoms of APS.

EXAMPLES

In order to make the compositions of the present invention and methods of their use clearer, the following examples are presented. These examples are only for illustrative purposes and should not be interpreted in any way as limitations on the compositions and uses of this invention.

Example 1

Design of a Dimeric Inhibitor

The first LA module from ApoER2 (A1) binds domain V of β2GPI with 1 mM affinity (Lee et al., *Structure* 18:366-376, 2010). In order to target a multivalent β2GPI formed by anti-β2GPI antibodies, we made a dimeric inhibitor (SEQ ID NO: 1) that includes two A1 modules (SEQ ID NOs: 2 and 3) covalently connected by a linker. To allow largely unrestricted relative motion of two A1 modules in the A1-A1 molecule, we used a flexible linker Gly-Ser-Ser-Gly (SEQ ID NO: 4) to connect A1 modules. The use of this linker should not be interpreted as a limitation on the invention. Other linkers of equivalent structure and length can also be used (e.g., a linker that includes (Gly), where n=1 to 10 (e.g., n=1, 2, 3, 4, 5, 6, 7, 8, 9, or 10; SEQ ID NO: 5), (Ser), where n=1 to 10 (e.g., n=1, 2, 3, 4, 5, 6, 7, 8, 9, or 10; SEQ ID NO: 6), (Ala), where n=1 to 10 (e.g., n=1, 2, 3, 4, 5, 6, 7, 8, 9, or 10; SEQ ID NO: 7), (Gly-Ser), where n=1 to 10 (e.g., n=1, 2, 3, 4, 5, 6, 7, 8, 9, or 10; SEQ ID NO: 8), (Gly-Ser-Ser-Gly), where n=1 to 10 (e.g., n=1, 2, 3, 4, 5, 6, 7, 8, 9, or 10; SEQ ID NO: 9), (Gly-Ser-Gly), where n=1 to 10 (e.g., n=1, 2, 3, 4, 5, 6, 7, 8, 9, or 10; SEQ ID NO: 10), (Gly-Ser-Ser), where n=1 to 10 (e.g., n=1, 2, 3, 4, 5, 6, 7, 8, 9, or 10; SEQ ID NO: 11), (Gly-Ala), where n=1 to 10 (e.g., n=1, 2, 3, 4, 5, 6, 7, 8, 9, or 10; SEQ ID NO: 12), or any combination thereof. In extended conformation, the linker (e.g., the Gly-Ser-Ser-Gly linker) is capable of separating the A1 modules in A1-A1 by, e.g., 15 Å (e.g., separation in the range of 1 to 30 Å, more preferably 5 to 25 Å, e.g., 10, 11, 12, 13, 14, 15, 16, 17, 18, 19, 20, 21, 22, 23, 24, or 25 Å).

We expressed and purified A1-A1 using the same procedure that we have previously used for the expression and purification of other LA modules including A1 (see, e.g., Lee et al., *Structure* 18:366-376, 2010; Abdul-Aziz et al., *Biochemistry* 44:5075-5085, 2005; Beglov et al., *Proteins* 77:940-949, 2009; and Fisher et al., *Mol. Cell* 22:277-283, 2006; each of which is incorporated herein by reference in their entirety). Our previous analysis of different recombinantly expressed LA modules by solution NMR spectroscopy and crystallography demonstrated that the purified LA modules are properly folded, their structures are identical to the structures of these modules in full-length receptors and, in the presence of calcium, recombinant LA modules bind their ligands β2GPI, β2GPI-DV, RAP, and ApoE.

Because calcium is essential for the function of LA modules and the formation of native disulfide bonds (Blacklow, *Curr Opin Struct Biol* 17:419-426, 2007), we analyzed the folding of the dimeric molecule, A1-A1, in the presence and absence of calcium. We compared the oxidative refolding of A1-A1 to the refolding of A1, which yields a functional A1 module. The same quantities of the recombinant proteins were dialyzed in redox buffer containing either calcium or EDTA. After 36 hours (samples with A1) or 72 hours (samples with A1-A1) of refolding, the proteins were acidified with 0.1% TFA to stop the disulfide exchange and analyzed by a reversed-phase HPLC on an analytical C18 column. The A1 module contains six cysteine residues forming three disulfide bonds. In the presence of calcium, both A1 and A1-A1 converged to unique disulfide-bonded species out of many possibilities providing evidence that the presence of calcium guided formation of native disulfide bonds (see FIGS. 1A and 1B). For comparison, refolding of A1 and A1-A1 in the presence of EDTA yielded a distribution of multiple disulfide-bonded isomers.

Example 2

Figure 2:
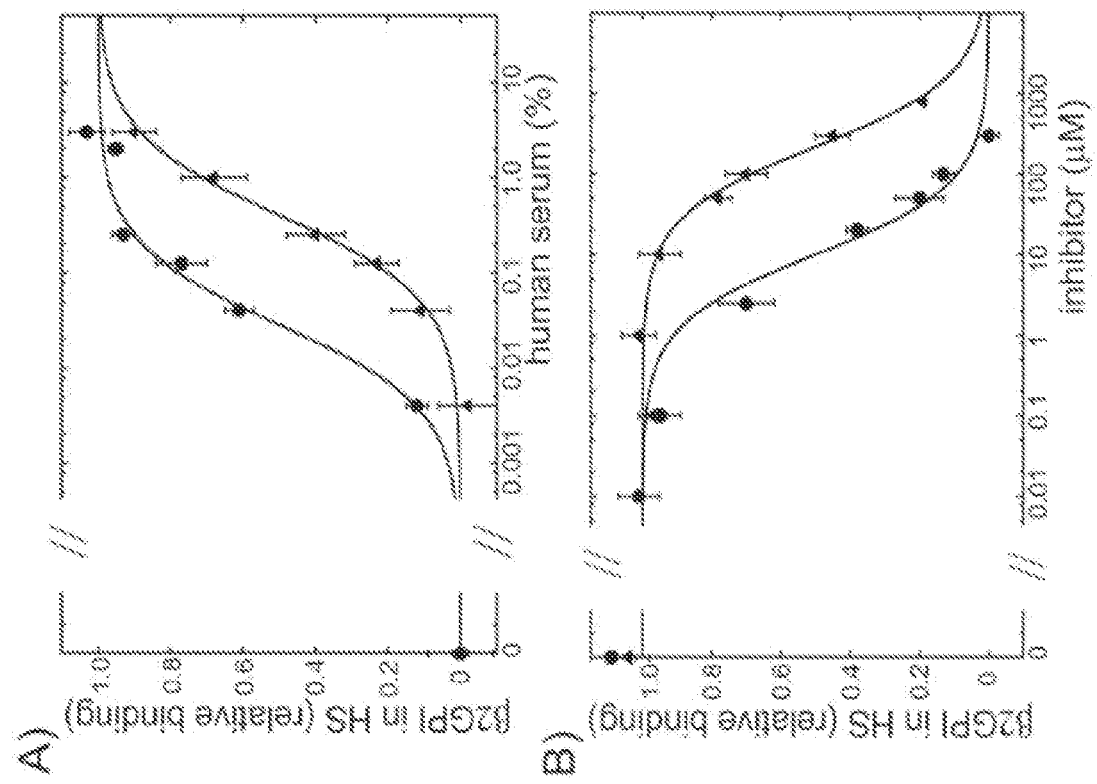
Figure 3:
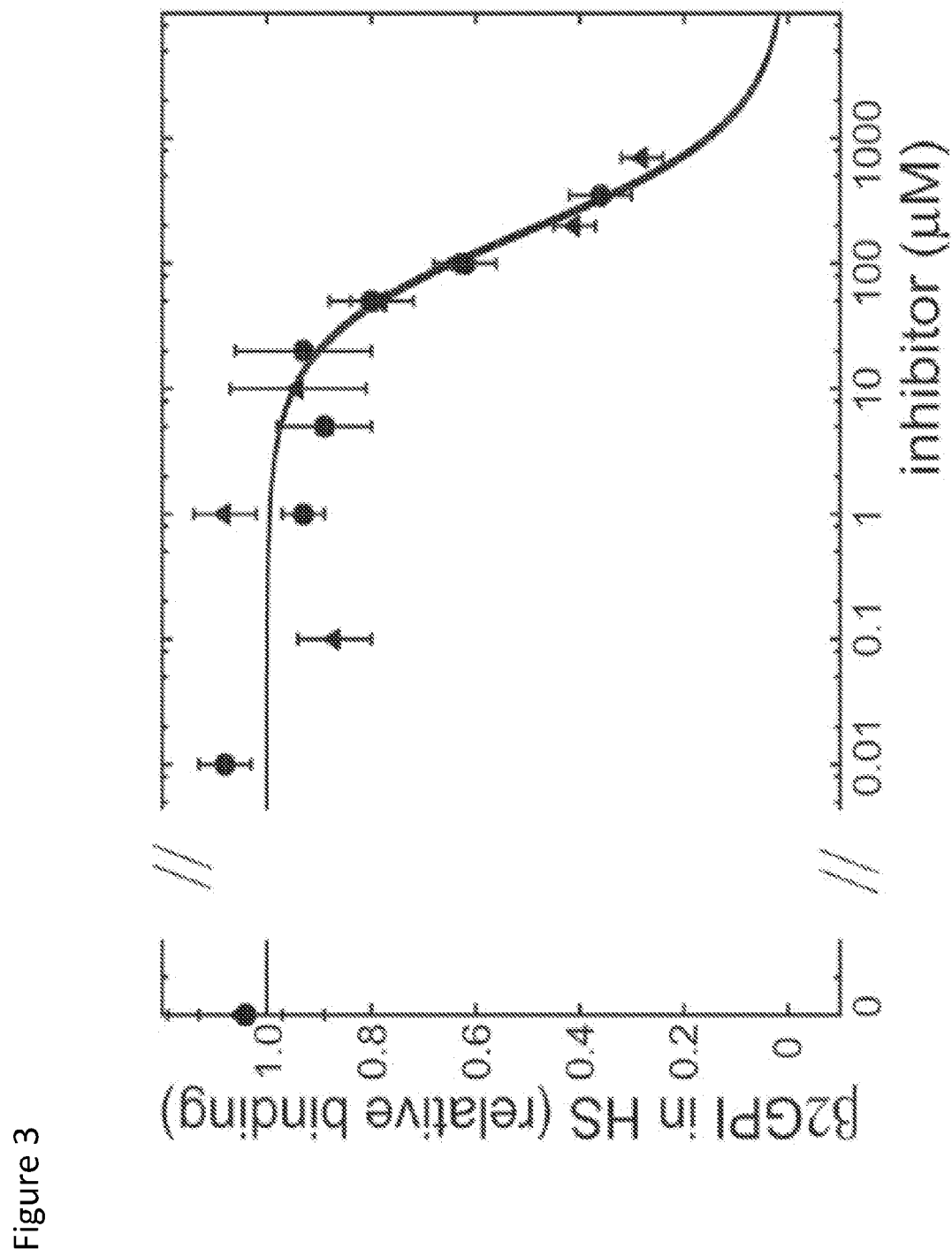
FIG. 3 is a graph showing inhibition of the binding of β2GPI in human serum to cardiolipin in the absence of anti-β2GPI antibodies. Inhibition curves measured for the dimeric inhibitor A1-A1 (circles; SEQ ID NO: 1) and monomeric inhibitor A1 (triangles; amino acids 12-47 of mature murine ApoER2, which corresponds to amino acids 2-37 of SEQ ID NO:1). On the plot, the data points at 50 μM and 100 μM of A1-A1 partially overlap with the data points at 50 μM and 100 μM of A1. To facilitate comparison, the measured $OD_{405}$ values and the binding curves were normalized to the maximum binding obtained from the fit of the raw data to a one-site inhibition model.

Comparison of the Dimeric Inhibitor A1-A1 with Monomeric A1. Inhibition of the Binding of β2GPI to Cardiolipin Anti-β2GPI antibodies create multivalent β2GPI/anti-β2GPI complexes that have pathological properties compared to pathologically inactive β2GPI monomers, which are normally present in plasma. The binding of β2GPI to anionic phospholipids in the presence of anti-β2GPI antibodies is one of the pathological mechanisms leading to APS and its symptoms, e.g., thrombosis and pregnancy losses. We compared the dimeric inhibitor, A1-A1, to monomeric A1 on the inhibition of binding of β2GPI/anti-β2GPI antibody complexes to cardiolipin. First, we used pooled normal human serum as a source of β2GPI. The majority of the β2GPI molecules in serum is in the circular form (Agar et al., *Blood,* 2010). To select the appropriate concentration of β2GPI for the inhibition studies, we measured the binding of β2GPI to cardiolipin (FIG. 2A). To create β2GPI/anti-β2GPI complexes, anti-β2GPI antibodies at constant concentration were added to β2GPI before the samples were applied to cardiolipin. The presence of anti-β2GPI antibodies significantly enhanced the binding of β2GPI to cardiolipin reaching the half-maximal binding at 0.028±0.004% and 0.40±0.05% of serum in the presence and in the absence of anti-β2GPI antibodies, respectively. We then compared the efficiency of A1-A1 and A1 for the inhibition of the binding of β2GPI in serum to cardiolipin in the presence of anti-β2GPI antibodies (FIG. 2B). 0.04% of human serum, which is in the linear region of the binding curve, was incubated on a cardiolipin-coated surface in the presence of anti-β2GPI antibodies and the inhibitors. In the presence of anti-β2GPI antibodies, the dimeric molecule, A1-A1, inhibited the binding to cardiolipin of β2GPI in serum much stronger than monomeric A1. The half-maximal inhibition in the presence of anti-β2GPI antibodies was achieved at 10±2 μM of A1-A1 and 218±21 μM of A1. Also, we measured how A1-A1 and A1 inhibited the binding of β2GPI in serum in the absence of anti-β2GPI antibodies (FIG. 3). A 1% solution of human serum was titrated with A1-A1 or A1 and β2GPI bound to cardiolipin was subsequently detected with anti-β2GPI antibodies. In the absence of anti-β2GPI antibodies, both A1-A1 and A1 were equally ineffective in inhibition of β2GPI. The concentration of the inhibitors at 50% inhibition of β2GPI was 189±34 μM for A1-A1 and 176±37 μM for A1. In sum, the efficiency of A1-A1 to inhibit the binding of β2GPI in serum to cardiolipin was significantly stronger in the presence of anti-β2GPI antibody than in the absence of antibodies. A1-A1 was more effective than A1 in inhibition of β2GPI in serum in the presence of anti-β2GPI antibodies. The inhibition efficiency of the monomeric A1 was practically the same and weak regardless of the presence or absence of anti-β2GPI antibodies.

Figure 4:
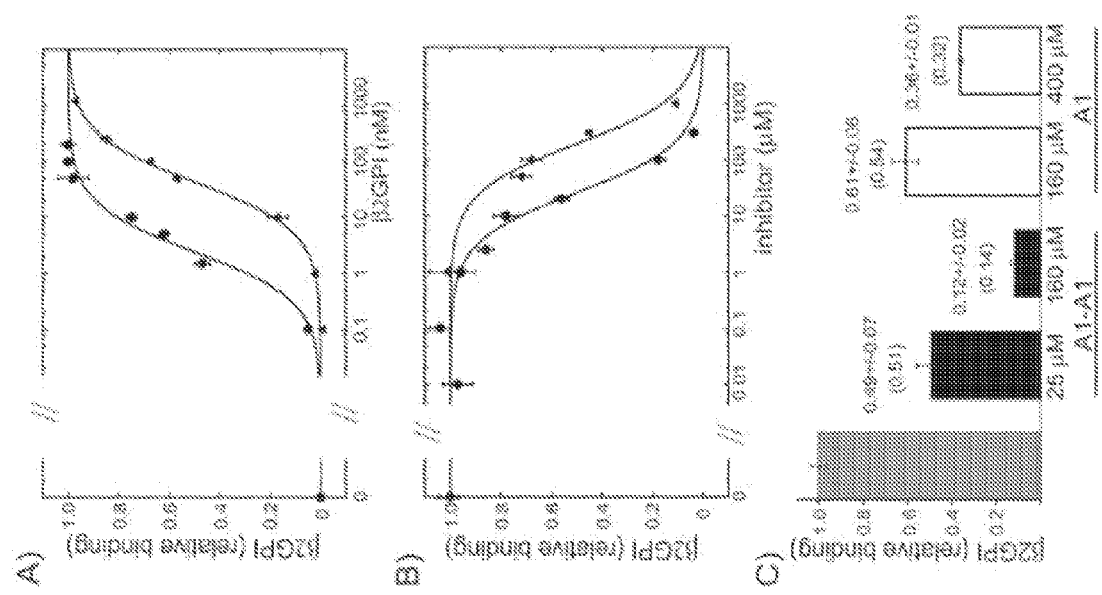
FIGS. 4A-4C are graphs showing the binding of purified β2GPI to cardiolipin.
Figure 5:
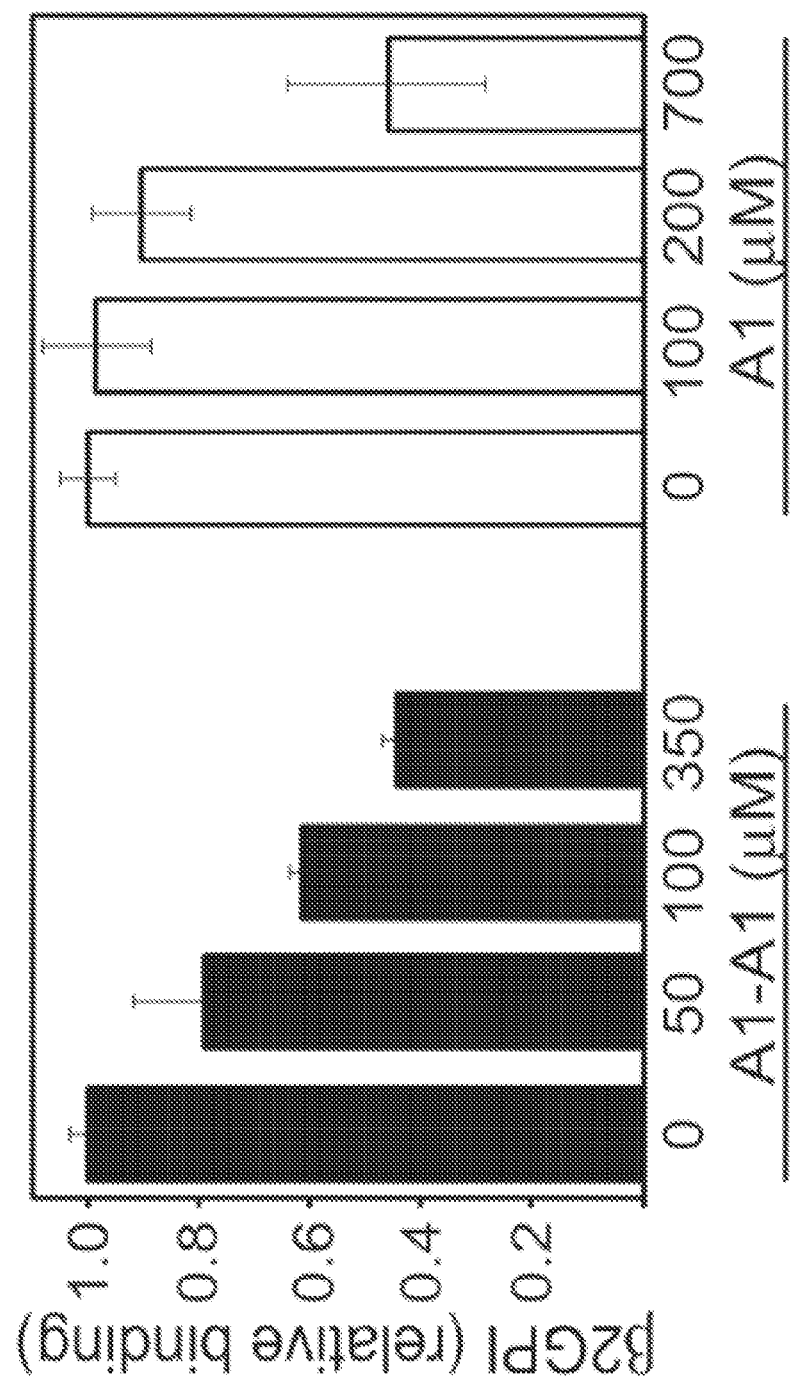
FIG. 5 is a graph showing inhibition of the binding of purified β2GPI to cardiolipin by A1-A1 (SEQ ID NO: 1) and A1 (amino acids 12-47 of mature murine ApoER2, which corresponds to amino acids 2-37 of SEQ ID NO:1) in the absence of anti-γ2GPI antibodies. The purified β2GPI bound to cardiolipin in the absence of anti-β2GPI antibody with increasing amounts of A1-A1 (black bars) and A1 (white bars). The $OD_{405}$ values were normalized to $OD_{405}$ measured in the absence of inhibitor.

Next, we analyzed how A1-A1 and A1 inhibit the binding of purified β2GPI to cardiolipin. Closed and extended conformations of β2GPI can be interconverted by altering of pH and concentrations of NaCl in the buffer (Agar et al. *Blood*, 2010), suggesting that the conformation of purified β2GPI may depend on the purification procedure. We used β2GPI purified from human plasma available from Haematologic Technologies, Inc. and analyzed the binding and inhibition of the binding of purified β2GPI by A1-A1 and A1 in the presence and in the absence of anti-β2GPI antibodies. The half-maximal binding was achieved at 2.4±0.4 nM and 43±4 nM of the purified β2GPI in the presence and in the absence of anti-β2GPI antibodies, respectively (FIG. 4A). We incubated 10 nM of β2GPI with various concentrations of the dimeric, A1-A1, and monomeric, A1, inhibitors in the presence of anti-β2GPI antibodies. Similarly to what we observed for β2GPI in serum, A1-A1 was more effective in inhibition of the binding of β2GPI to cardiolipin in the presence of anti-β2GPI antibodies. The fit of the titration data to the one-site inhibition model resulted in 26±3 μM of A1-A1 and 191±34 μM of A1 at half-maximal inhibition of purified β2GPI in the presence of anti-β2GPI antibodies (FIG. 4B). In a separate experiment, we measured the inhibition of β2GPI in the presence of antibodies and compared the measured values to values predicted by the fit of the titration data (FIG. 4C). The measured values were close to those expected from the fit, additionally confirming that in the presence of anti-β2GPI antibodies a much lower concentration of A1-A1 was required to inhibit 50% of the binding of purified β2GPI to cardiolipin compared to A1. In the absence of anti-β2GPI antibodies, both A1-A1 and A1 only weakly inhibited the binding of the purified β2GPI to cardiolipin (FIG. 5). Similarly to what we observed for β2GPI in serum, the binding of purified β2GPI to cardiolipin in the presence of anti-β2GPI antibodies was inhibited more strongly by the dimeric inhibitor A1-A1 than by A1. Both, A1-A1 and A1, were ineffective in the inhibition of β2GPI in the absence of anti-β2GPI antibodies.

Example 3

Crystal Structure of the Individual Recombinantly Expressed Domain V of β2GPI (β2GPIDV)

B2GPI binds anionic phospholipids and the A1 modules by its domain V (Hunt et al., *J Immunol* 152:653-659, 1994; Mehdi et al., *Eur J Biochem* 267:1770-1776, 2000; Sheng et al., *J Immunol* 157:3744-3751, 1996; Lummel et al., *J Biol Chem* 280:36729-36736, 2005; Lee et al., *Structure* 18:366-376, 2010). We used x-ray crystallography to demonstrate that the structure of the isolated domain V is identical to the structure of this domain in the extended conformation of β2GPI. Two crystal structures of a full-length β2GPI in the PDB database are solved for β2GPI in extended Conformation (Bouma et al., *Embo J.* 18:5166-5174, 1999; and Schwarzenbacher et al., *Embo J.* 18:6228-6239, 1999). In the extended conformation, domain V at the C-terminus of β2GPI forms essentially no contacts with the adjacent domain IV. There are no glycosylation sites in β2GPI-DV that could affect its function and the nearest glycosylation site in domain IV is far from domain V in the 3D structure of β2GPI. These observations suggest that the individual domain V dissected from the full-length β2GPI will function as domain V in the extended form of β2GPI.

Figure 6:
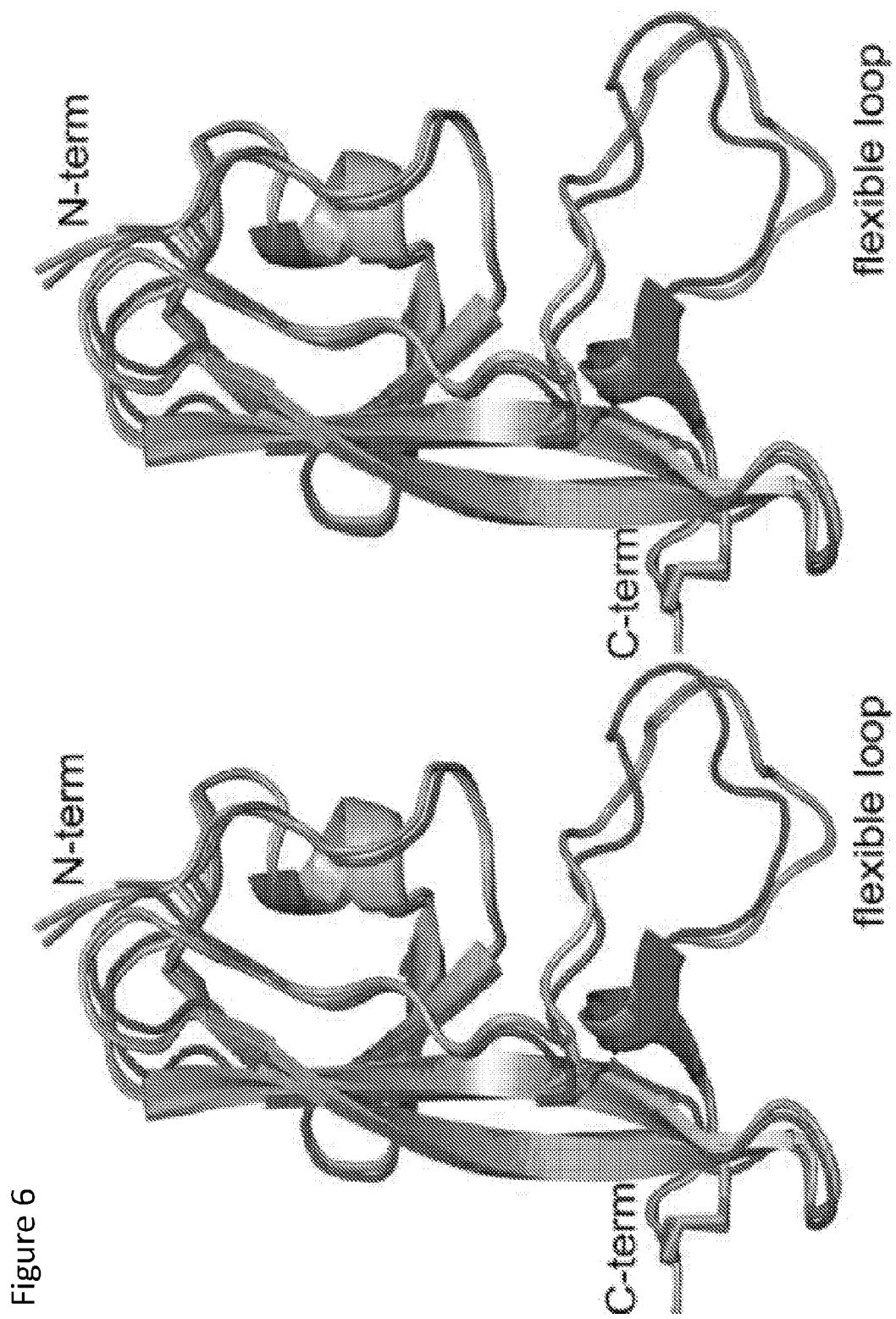
FIG. 6 is a stereoview of the crystal structure of the isolated domain V of β2GPI. Backbone superposition of the structures of β2GPI-DV chain A (green) with the structure of β2GPI-DV chain B (blue) and the crystal structure of domain V from the full-length β2GPI (PDB ID 1C1Z) (red). A flexible loop in the C-terminal part of domain V and N- and C-termini of the domain are labeled.

We confirmed that the isolated domain V has the same structure as domain V in the extended form of the full-length β2GPI by solving its crystal structure to 1.9 Å resolution (Table 1). The two molecules of β2GPI-DV in the asymmetric unit of the crystal, chains A and B, have nearly identical structures with backbone RMS deviation of 0.23 Å. Superposition of the backbone atoms in domain V in the full-length β2GPI (PDB ID 1C1Z, residues from 244 to 326) onto the structure of the isolated domain V, β2GPI-DV, resulted in RMSD of 1.04 Å and 0.97 Å for chains A and B, respectively. As illustrated by FIG. 6, the backbone conformation of individual β2GPI-DV is nearly identical to the structure of domain V in the full-length β2GPI. The largest difference between the structures is localized to a loop at the C-terminal part of domain V. Experimental data strongly suggests that this loop is flexible in the native protein. For example, the residues from 311 to 317 comprising this loop are not defined in one of the crystal structures of the full-length β2GPI (PDB ID 1QUB) (Bouma et al., *Embo J.* 18:5166-5174, 1999) and have large values of B-factors in the other (PDB ID 1C1Z) (Schwarzenbacher et al., *Embo J.* 18:6228-6239, 1999). Also, the residues in the loop are either weak or missing from the NMR spectrum of β2GPI-DV in solution reflecting its internal flexibility (Lee et al., *Structure* 18:366-376, 2010). The structural similarity between the isolated domain V and domain V in the crystal structure of the extended form of β2GPI provides convincing evidence that the isolated recombinant domain V of β2GPI mimics domain V in the extended form of β2GPI.

TABLE 1

Crystallographic Statistics

Data Statistics

| | |
|---|---|
| Beamline | NSLS X29 |
| Wavelength (Å) | 1.075 |
| Space group | P1 |
| Cell parameters | |
| (Å) | a = 24.29 b = 38.09 |
| | c = 49.51 |
| (°) | α = 93.83 β = 102.65 |
| | γ = 90.09 |
| Resolution range (Å)[a] | 38.0-1.9 (2.0-1.9) |
| Total number of observations[a] | 48247 (7052) |
| Total number of unique[a] | 12817 (1850) |
| Completeness (%)[a] | 94.3 (93.8) |
| I/I(σ)[a] | 12.6 (4.5) |
| Multiplicity[a] | 3.8 (3.8) |

TABLE 1-continued

Crystallographic Statistics

| | |
|---|---|
| $R_{merge}$ (%)[a] | 6.1 (26.7) |
| Molecules in asymmetric unit | 2 |

Refinement Statistics

| | |
|---|---|
| Free reflections (%) | 5 |
| $R_{work}$ (%) | 18 |
| $R_{free}$ (%) | 21.8 |
| Protein atoms including H | 2812 |
| Waters | 110 |

RMSD from Ideal Geometry

| | |
|---|---|
| Bond angles (°) | 1.5 |
| Bond lengths (Å) | 0.015 |
| Chirality | 0.102 |
| Planarity | 0.007 |
| Dihedral | 13.4 |

Ramchandran Plot number of residues in:

| | |
|---|---|
| Preferred regions | 159 (96.95%) |
| Allowed regions | 5 (3.05%) |
| Disallowed regions | 0 |

[a]Values in parenthesis correspond to the highest resolution shell

Example 4

Comparison of the Dimeric Inhibitor A1-A1 with Monomeric A1. Inhibition of the Binding of the Individual Domain V of β2GPI to Cardiolipin in the Presence of the Dimerization Antibodies To analyze how A1-A1 and A1 inhibit the binding of the extended form of β2GPI to cardiolipin, we used purified domain V of β2GPI (β2GPI-DV). We introduced a peptide tag at the N-terminus of β2GPI-DV and used an antibody directed to the tag to form dimeric β2GPIDV/antibody complexes. We have previously demonstrated that the A1 module binds to the C-terminal part of β2GPI-DV (Lee et al., *Structure* 18:366-376, 2010), and therefore the N-terminal peptide tag on β2GPI-DV and the bound anti-tag antibody will not interfere with the binding of the A1 modules to β2GPI-DV.

Figure 7:
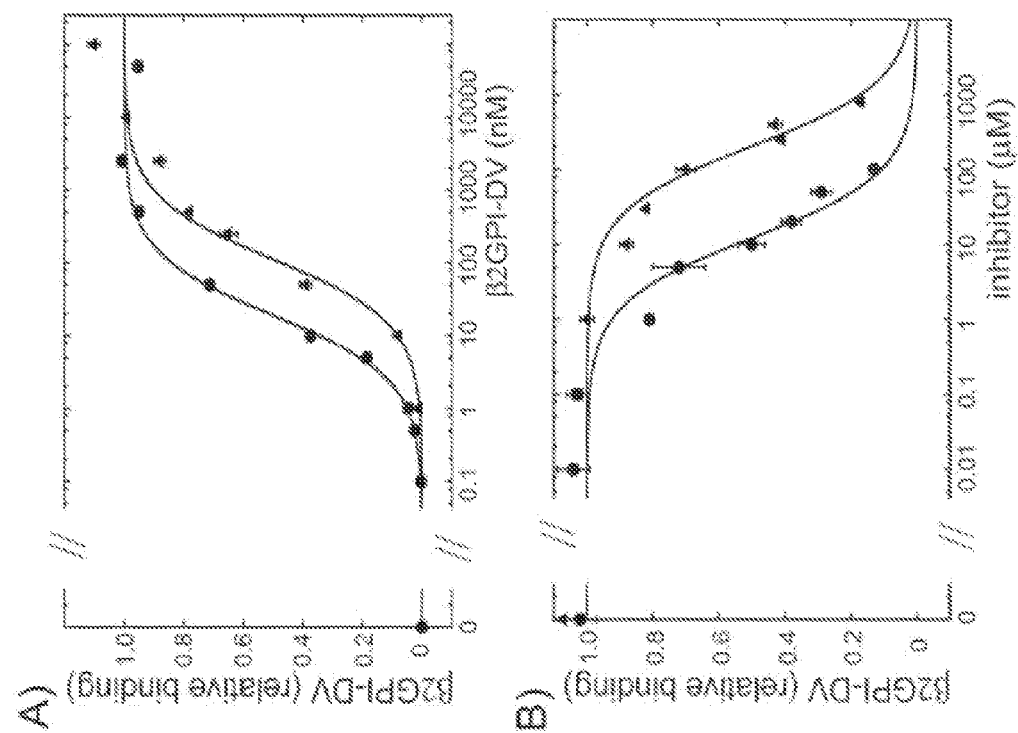
FIGS. 7A and 7B are graphs showing binding of the individual domain V of β2GPI (β2GPI-DV) to cardiolipin.

As in the case of the full-length β2GPI, the presence of divalent β2GPI-DV/antibody complexes increased the attachment of β2GPI-DV to cardiolipin (FIG. 7A). The fit of the binding data to a one-site model resulted in 19±1 nM of β2GPI-DV and 112±21 nM of β2GPI-DV in the presence and in the absence of anti-tag antibodies. When 30 nM of β2GPI-DV in the presence of anti-tag antibody was incubated with the inhibitors, the half-maximal inhibition was reached at 12±2 μM of A1-A1 and 204±33 μM of A1 (FIG. 7B). As we observed for the inhibition of the binding of β2GPI in human serum and purified β2GPI to cardiolipin-coated surfaces, the isolated domain V was inhibited much stronger by the dimeric inhibitor A1-A1 compared to monomeric A1 in the presence of dimeric β2GPI-DV/anti-tag antibody complexes.

Example 5

Figure 8:
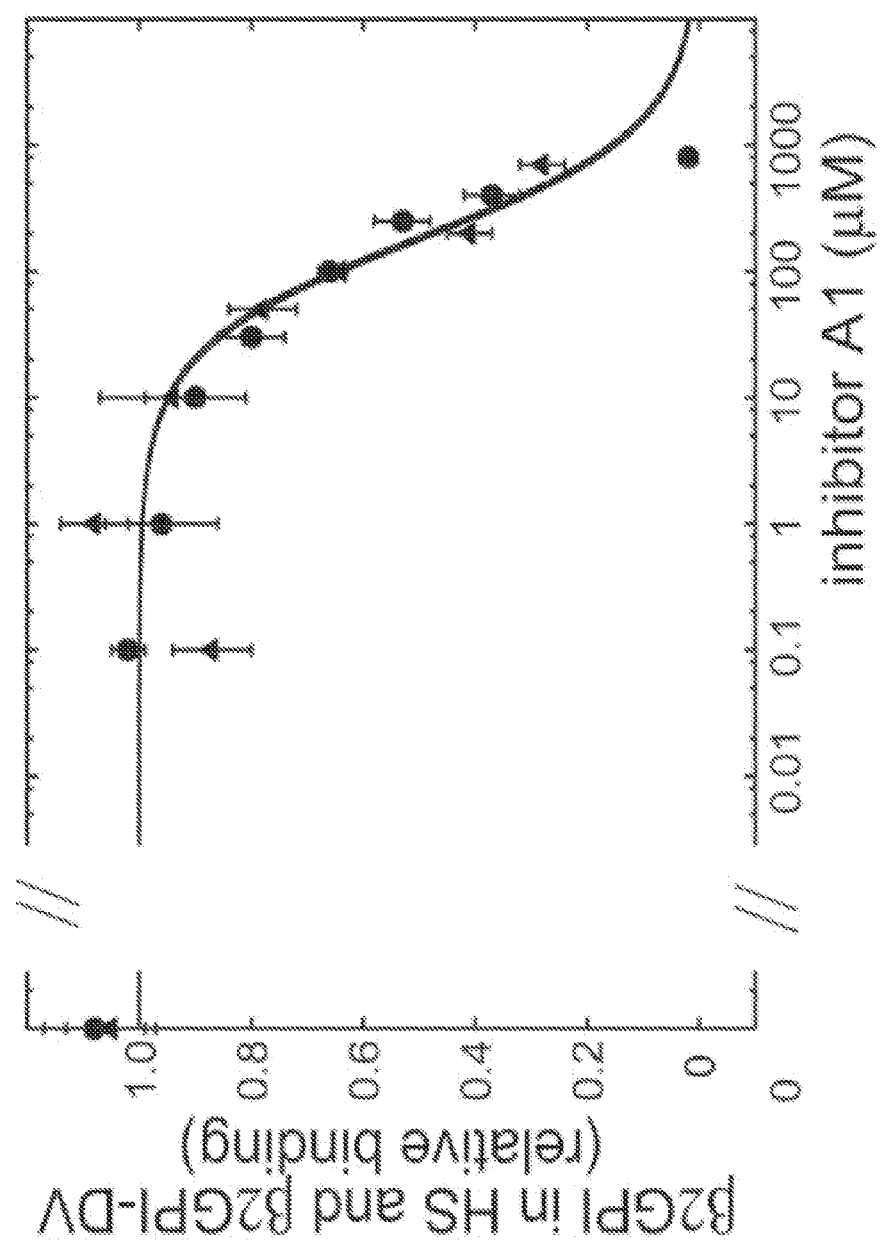
FIG. 8 is a graph showing a comparison of the inhibition of β2GPI in serum with the inhibition of the isolated domain V in the absence of dimerization antibodies by monomeric A1. Inhibition of the binding of γ2GPI-DV by A1 (circles; amino acids 12-47 of mature murine ApoER2, which corresponds to amino acids 2-37 of SEQ ID NO:1); inhibition of the binding of μ2GPI in serum by A1 (triangles).

Comparison of β2GPI in Human Serum with the Isolated Domain V of β2GPI. Inhibition of the Binding to Cardiolipin by a Monomeric A1 in the Absence of Antibodies We investigated if the binding of two forms of β2GPI, circular and extended, to cardiolipin is inhibited similarly by A1. We analyzed the inhibition of the monomeric molecules, β2GPI in serum and the isolated domain V, by monomeric A1. The majority of β2GPI in normal human serum is in a circular conformation (Agar et al., *Blood,* 2010). The isolated domain V mimics domain V in the extended form of β2GPI. The same concentration of A1 was required to inhibit 50% of the binding of β2GPI in human serum and the individual domain V of β2GPI (FIG. 8). The concentration of A1 at half-maximal inhibition was 176±37 μM for β2GPI in serum and 188±44 μM for domain V. This observation demonstrates that A1 binds circular and extended β2GPI with the same affinity suggesting that the binding site for A1 is not obscured in the circular form of β2GPI.

Example 6

Stability of the A1-A1 inhibitor in human serum at 37° C.

Figure 9:
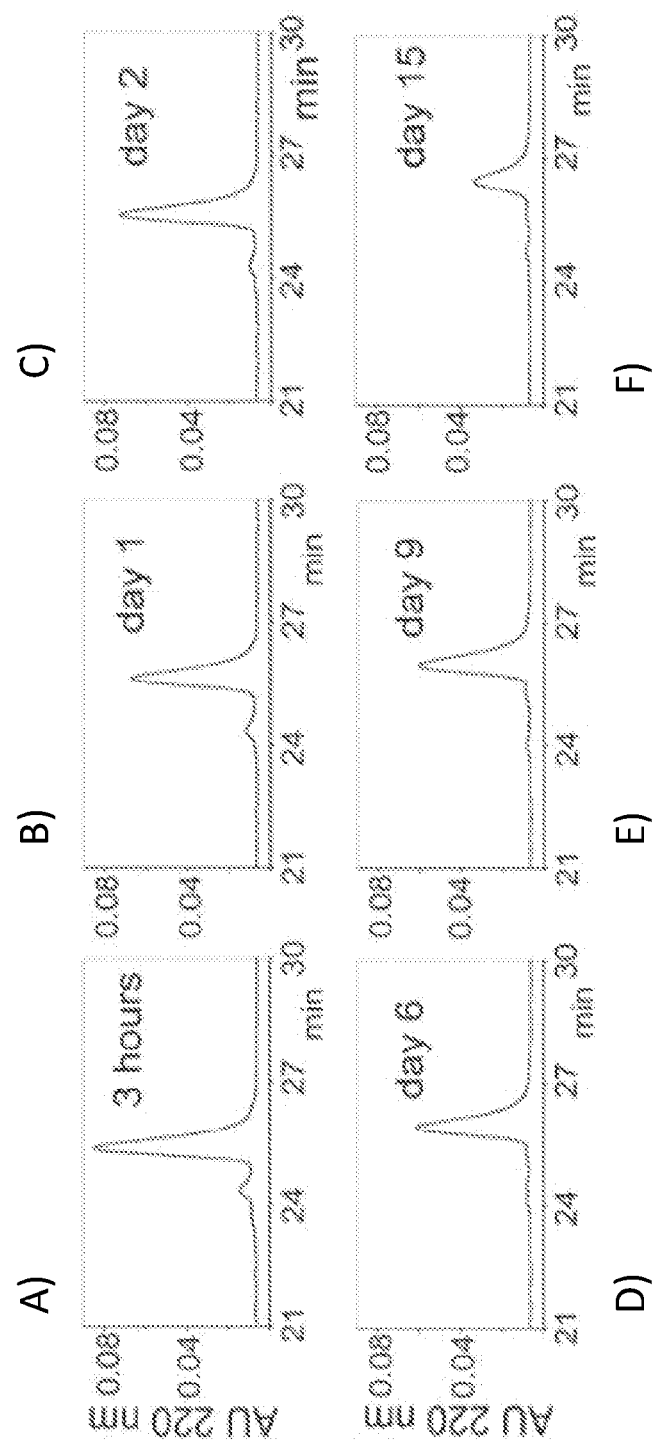

To evaluate the susceptibility of the A1-A1 inhibitor to degradation by serum proteases, we incubated A1-A1 in serum at 37° C. Degradation of A1-A1 was monitored by the reversed-phase HPLC by comparing the peak corresponding to the intact A1-A1 on chromatograms collected at different time intervals. The amount of A1-A1 that remained in serum was calculated from the area under the eluded peak. More than 35% of A1-A1 remained in serum after 15 days of incubation at 37° C., indicating that A1-A1 has a favorable stability in serum (FIG. 9).

Discussion

The work reported here examines the effectiveness of a novel dimeric inhibitor A1-A1 to interfere with the binding of β2GPI/anti-β2GPI antibody complexes to anionic phospholipids compared to monomeric A1. The dimeric inhibitor consists of two identical ligand-binding LA modules from ApoER2 (A1) connected by a flexible peptide linker Biophysical characterization of A1-A1 by reverse-phased chromatography confirmed that A1-A1 is correctly folded in a calcium-dependent manner Recently, we determined that the bound A1 module prevents the association of β2GPI with anionic phospholipids (Lee et al., *Structure* 18:366-376, 2010). Present studies confirmed our previous observations suggesting that the dimeric A1 inhibitor interferes with two pathologically important interactions: the binding of β2GPI/antibody complexes to anionic phospholipids and to ApoER2, a lipoprotein receptor on platelets (Rand et al., *Lupus* 19:460-469, 2010; and van Os et al. *Hämostaseologie* 30:139-143, 2010).

Normally, β2GPI circulates in the blood plasma as a monomer. Anti-β2GPI antibodies in patients with antiphospholipid syndrome (APS) create multivalent β2GPI complexes that have much stronger affinity for anionic phospholipids and lipoprotein receptors than the monomeric β2GPI (Pennings et al., *J. Thromb. Haemost.* 4:1680-1690, 2006; and Willems et al., *Biochemistry* 35:13833-13842, 1996). Because β2GPI/antibody complexes expressing dimeric β2GPI have prothrombotic properties, in contrast to monomeric pathologically inactive β2GPI, we designed a dimeric inhibitor. The dimeric molecule A1-A1 preferentially targets multivalent pathological β2GPI/anti-β2GPI antibody complexes leaving monomeric β2GPI, which is abundant in plasma, practically unaffected.

We compared the dimeric inhibitor A1-A1 to monomeric A1 on the inhibition of the binding of β2GPI to anionic phospholipids in the presence and in the absence of anti-β2GPI antibodies. To evaluate the binding of A1-A1 and A1 to β2GPI, we used different preparations of β2GPI, such as β2GPI in normal human serum, β2GPI purified from human plasma, and recombinant domain V of β2GPI. All of these preparations of β2GPI can bind A1. β2GPI is a flexible molecule that can adopt a circular (Agar et al., Blood, 2010) and extended conformation (Bouma et al., *Embo J.* 18:5166-5174, 1999; Schwarzenbacher et al., *Embo J.* 18:6228-6239, 1999; and Hammel et al., *J. Mol. Biol.* 321:85-97, 2002). β2GPI in plasma is predominantly in a circular form (Agar et al., Blood, 2010) and the individual domain V closely resembles domain V in the extended conformation of β2GPI, as we demonstrated by the x-ray crystallography.

Figure 10:
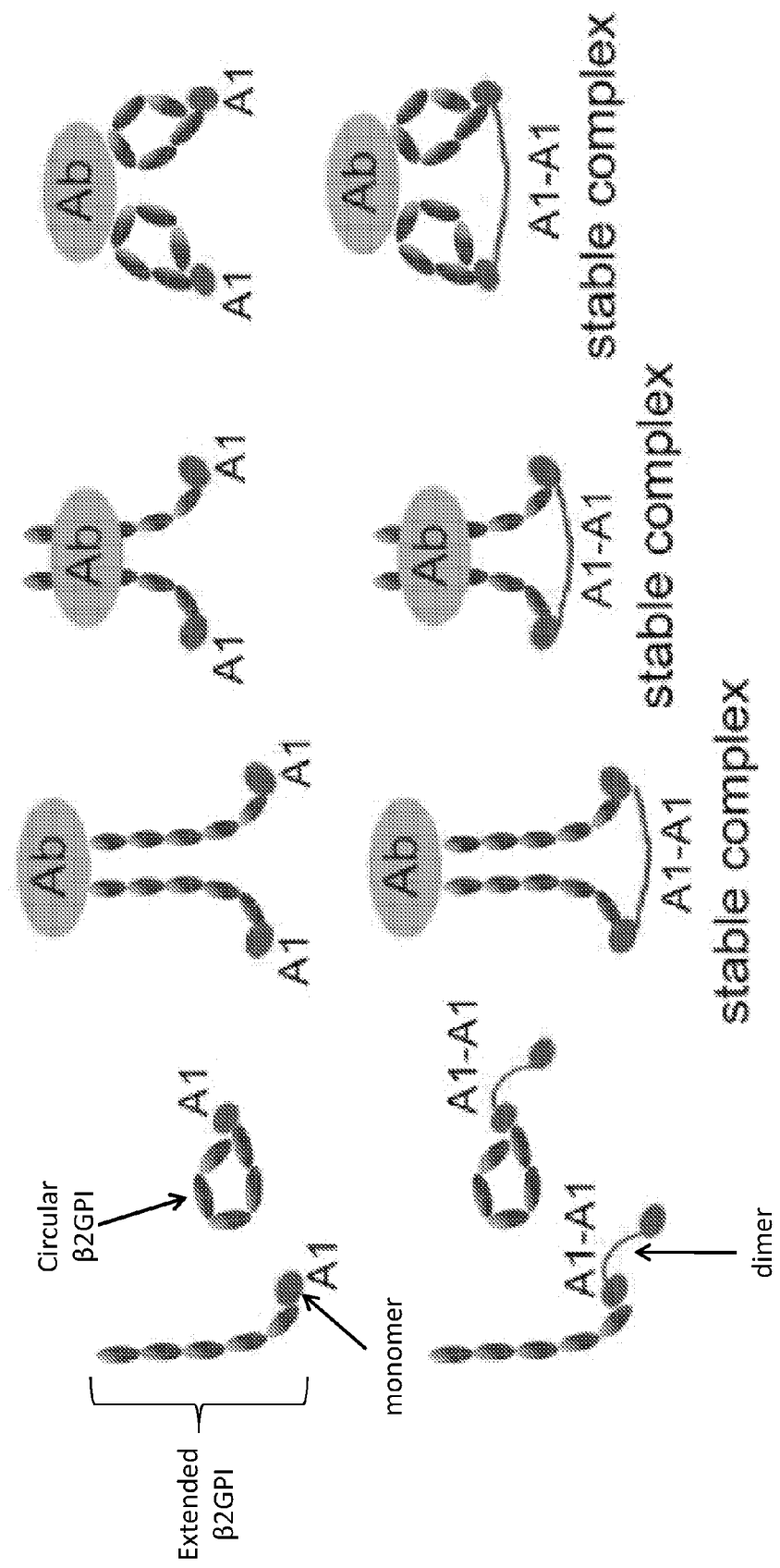

We determined that, regardless of the source of β2GPI, 1) A1-A1 is much more efficient in inhibition of the binding of β2GPI/antibody complexes to anionic phospholipids than A1 and 2) the inhibition of the binding of monomeric β2GPI to anionic phospholipids by either A1-A1 or A1 is practically identical and weak. We also observed that the inhibition of both β2GPI in serum and the individual domain V by A1 is identical in the absence of dimerization antibodies, suggesting that A1 binds the circular and extended forms of β2GPI with the same affinity. Therefore, the binding site for A1 is not obscured on the circular form of β2GPI. Anti-β2GPI antibodies in patients with APS are heterogeneous and their epitopes are scattered over domains I to IV of β2GPI (van Os et al. *Hämostaseologie* 30:139-143, 2010; and Giles et al., *Arthritis Rheum.* 48:2111-2121, 2003). Some APS antibodies might bind circular β2GPI and some APS antibodies might need an extended β2GPI to have their epitopes exposed. Also, the binding of high affinity antibodies can convert circular β2GPI to extended (Agar et al., Blood, 2010). Our results demonstrated that when β2GPI, whether circular or extended, is dimerized by anti-β2GPI antibodies, it is more strongly inhibited by A1-A1 than by monomeric A1 by forming stable β2GPI/anti-β2GPI/A1-A1 complexes (FIG. 10).

In our previous work, we have shown that LA modules from all lipoprotein receptors bind to the same site on β2GPI-DV (Lee et al., *Structure* 18:366-376, 2010). Therefore, A1-A1 inhibits the binding of β2GPI/antibody complexes not only to ApoER2, but to other lipoprotein receptors as well. Whether other lipoprotein receptors besides ApoER2 contribute to the pathology of APS awaits further investigation.

The A1 module is a well-structured small protein domain which conformation is maintained by three disulphide bonds and a bound calcium ion. We measured in vitro the serum stability of A1-A1. About 35% of A1-A1 remained intact after incubation in serum at 37° C. for more than two weeks, indicating that A1-A1 might have favorable pharmacokinetic properties. Given that LA modules are naturally expressed, the A1-A1 inhibitor is unlikely to be immunogenic.

Taken together, our results suggest that A1-A1 and the related compositions of the present invention are effective inhibitors that interfere with the binding of β2GPI/antibody complexes to anionic phospholipids and lipoprotein receptors.

We believe the approach of using a dimeric inhibitor that blocks β2GPI in the pathological multivalent β2GPI/anti-β2GPI complexes holds significant promise in the treatment of APS or one or more of its symptoms. In these studies, we are inhibiting a well characterized binding site for lipoprotein receptors on β2GPI, instead of preventing the binding of antibodies to β2GPI, which are highly heterogeneous in APS patients. Our approach to target the dimerized β2GPI with a dimeric inhibitor could be applied to other pathologically important interactions of β2GPI/antibody complexes.

In conclusion, we developed and tested a novel dimeric inhibitor of the β2GPI/antibody complexes. This dimeric inhibitor preferentially targets β2GPI dimerized by anti-β2GPI antibodies compared to pathologically inactive monomeric β2GPI. It prevents the binding of β2GPI/antibody complexes to anionic phospholipids and ApoER2, and thus can be used to treat or APS and one or more of its symptoms (e.g., thrombosis and pregnancy-related complications complications).

Materials and Methods:

Protein Expression and Purification

Monomeric A1 is a fragment of mouse ApoER2 (residues 12-47 from the mature protein). The dimeric inhibitor, A1-A1, was constructed to contain two A1 fragments connected by a Gly-Ser-Ser-Gly linker. A1 and A1-A1 containing an extra N-terminal Ala and C-terminal Glu-Ala residues were expressed in *E. coli* as TrpLE fusion proteins and purified from inclusion bodies essentially as previously described (North et al., *Biochemistry* 39:2564-2571, 2000). Domain V of β2GPI (residues 244-326), was subcloned into a pET15b vector (Novagen). The encoded protein has an N-terminal histidine tag followed by the sequence recognized by the Tobacco Etch Virus (TEV) protease so that the tag can be removed. To make the domain V of β2GPI recognized by antibodies directed to an HA peptide, the HA sequence, YPY-DVPDYA, was introduced at the N-terminus of domain V right after the TEV cleavage site. Domain V with and without the peptide tag was expressed in *E. coli*, recovered from inclusion bodies, cleaved with TEV and refolded by dialysis at 4° C. under conditions permitting disulfide exchange before final purification by reversed-phase HPLC on a C18 column. Protein concentrations were calculated from the measured absorbance of samples at 280 nm using extinction coefficients from the output of ExPASy Protparam tool. A full-length β2GPI was purchased from Haematologic Technologies, Inc. Concentrations of β2GPI were calculated using an extinction coefficient at 280 nm $E^{1\%}$ of 10 and molecular weight of 54200, as suggested by the supplier.

Crystallization, Data Collection and Structure Determination of β2GPI-DV

Initial crystallization condition was determined in crystallization screen performed at the Hauptman-Woodward Medical Research Institute (Luft et al., *J. Struct. Biol.* 142:170-179, 2003). The best crystal of β2GPI-DV was obtained at room temperature in hanging drop by combining 1 μL of β2GPI-DV (7 mg/ml in 20 mM HEPES, pH 7.0) with 1 μL of reservoir solution containing 100 mM ammonium sulfate, 40% PEG 1500, 100 mM bis-Tris, pH 7.2. The reservoir solution supplemented with 20% glycerol was used as cryoprotectant. Data were collected from a single crystal at beamline X29A of Brookhaven National Laboratories (NSLS). The crystals belong to the space group P1 with two molecules of β2GPI-DV per asymmetric unit and a solvent content of 45%. Data were processed with MOSFLM (Leslie et al., *Acta Crystallogr. D Biol. Crystallogr.* 62:48-57, 2003). A total of 5% of reflections were excluded and used for $R_{free}$ calculations. The structure was solved by molecular replacement with PHASER (McCoy et al., *J. Appl. Crystallogr.* 40:658-674, 2007) using coordinates of domain V extracted from the crystal structure of β2GPI (PDB ID 1C1Z). The initial model determined by PHASER was adjusted with the program COOT (Emsley et al., *Acta Crystallogr. D Biol. Crystallogr.* 60:2126-2132, 2004) and refined using the program REF-MAC5 (Murshudov et al., *Acta Crystallogr. D Biol. Crystallogr.* 53:240-255, 1997). The final refinement was performed with PHENIX software suit (Adams et al., *Acta Crystallogr. D Biol. Crystallogr.* 66:213-221, 2010).

Assay for the Binding and Inhibition of the Binding of β2GPI and β2GPI-DV to a Cardiolipin-Coated Surface Cardiolipin-coated 96 well plates available as part of the ImmunoWELL cardiolipin IgG test kit (GenBio) were blocked with 0.5% of skim milk and 2% BSA in 20 mM Tris, 100 mM NaCl, 2 mM CaCl$_2$, pH 7.4. The assay buffer contained 20 mM Tris, 100 mM NaCl, 2 mM CaCl$_2$, pH 7.4 with 2% BSA and the wash buffer was 20 mM Tris, 100 mM NaCl, 2 mM CaCl$_2$, pH 7.4. When the purified β2GPI (Haematologic Technologies, Inc.) was used in experiments, 27 mM glycine was added to the assay buffer to account for glycine present in the stock solution of β2GPI. β2GPI bound to cardiolipin was detected with peroxidase-conjugated anti-β2GPI antibodies (Cedarlane, CL20021HP, 2 mg/ml) diluted 1:2500. To detect β2GPI-DV bound to cardiolipin, we used peroxidase-conjugated anti-HA antibody (Abcam, ab1265, 1 mg/ml) directed to HA epitope tag at the N-terminus of β2GPI-DV diluted 1:2500. The peroxidase activity of the bound antibodies was detected using 2-2'-azino-di-[3-ethyl-benzthizzoline]sulfonate (ABTS) chromogenic reagent by measuring OD at 405 nm. All measurements were done in triplicates and corrected to blank before data fitting. The blank contained all components except for β2GPI, serum, or β2GPI-DV. The binding and inhibition data was fitted to one-site models using the nonlinear least-squares Marquardt-Levenberg algorithm implemented in GNUPLOT program. The fits of the raw data and the titration data points were then normalized to the maximum binding determined from the fit to facilitate comparison.

For the binding studies, 50 μl of increasing concentrations of either β2GPI (Haematologic Technologies, Inc.), pooled normal human serum (Innovative Research), or the purified recombinant β2GPI-DV were applied to wells and incubated for 1 hour at room temperature. By "room temperature" is meant a temperature of about 5° C. to about 30° C., in particular from about 10° C. to about 27° C. (e.g., about 23-27° C.). After washing, anti-β2GPI or anti-HA antibody was added to wells and incubated for 1 hour at room temperature before detection. In the second set of experiments, samples containing various concentrations of β2GPI, pooled normal human serum or β2GPI-DV were first incubated for 1 hour at room temperature with the anti-β2GPI or anti-HA antibodies. Then, the samples were applied to cardiolipin, incubated for 1 hour, washed, and bound β2GPI or β2GPI-DV was detected.

For the inhibition studies, increasing concentrations of A1 or A1-A1 were added to a constant amount of β2GPI (50 nM), normal human serum (1%) or β2GPI-DV (130 nM) and incubated for 1 hour at room temperature. Then, 50 μl of the mixtures were incubated on wells for the additional 1 hour. After washing, 50 μl of either anti-β2GPI or anti-HA antibody was added to wells and incubated for 1 hour before detection. In the second set of experiments, 50 μl of samples containing increasing concentrations of A1 or A1-A1 and the constant amounts of either β2GPI (10 nM), normal human serum (0.04%) or β2GPI-DV (30 nM) were first incubated for 1 hour at room temperature with the anti-β2GPI or anti-HA antibodies. Then, samples were incubated on wells for an additional 1 hour and, after washing, the bound β2GPI/anti-β2GPI or β2GPI-DV/anti-tag antibody complexes were detected.

Measurements of the Stability of A1-A1 in Serum

Lyophilized A1-A1 purified by reversed-phase chromatography was dissolved in water and its concentration measured by absorbance at 280 nm. The required amount of A1-A1 (180 μg) was then lyophilized and, subsequently, dissolved in 360 μl of pooled normal human serum (Innovative Research). Serum with A1-A1 was sterile filtered through a 0.2 μm eppendorf centrifuge filter, divided into 40 μl samples and set for incubation at 37° C. At timed intervals, 900 μl of 10% acetonitrile with 0.1% TFA in water (buffer A) was added to a 40 μl sample of A1-A1 in serum. Filtered samples were analyzed by reversed-phase HPLC on a C18 column using a linear gradient of 0.1% per minute of buffer B (acetonitrile with 0.1% TFA) staring at 15 minutes from 16% of buffer B and monitored for 30 minutes.

Accession Numbers

Coordinates and structure factors have been deposited to the Protein Data Bank with accession number 3OP8.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

What is claimed is:

1. A method of treating antiphospholipid syndrome in a subject in need thereof comprising administering a composition comprising a polypeptide,
   wherein said polypeptide comprises a first low density lipoprotein (LDL) receptor-type A (LA) module, a second LA module, and a linker that joins said first LA module to said second LA module; and
   wherein said first LA module comprises a first A1 domain comprising an amino acid sequence with 85% or more sequence identity to the amino acid sequence of SEQ ID NO: 2, 3, 14, or 15, and said second LA module comprises a second A1 domain comprising an amino acid sequence with 85% or more sequence identity to the amino acid sequence of SEQ ID NO: 2, 3, 14, or 15, wherein said polypeptide specifically binds to first and second β2GPI monomers in a dimeric 32GPI/antibody complex.

2. The method of claim 1, wherein the amino acid sequence of said first LA module is the same as the amino acid sequence of said second LA module.

3. The method of claim 1, wherein said first A1 domain comprises an amino acid sequence with 85% or more sequence identity to the amino acid sequence of SEQ ID NO: 2 or 14 and said second A1 domain comprises an amino acid sequence with 85% or more sequence identity to the amino acid sequence of SEQ ID NO: 3 or 15.

4. The method of claim 3, wherein said linker comprises the amino acid sequence of any one of SEQ ID NOs: 4-12.

5. The method of claim 4, wherein said linker comprises the sequence of SEQ ID NO: 4.

6. The method of claim 1, wherein said polypeptide comprises a sequence having at least 85% sequence identity to SEQ ID NO: 1.

7. The method of claim 6, wherein said polypeptide comprises the sequence of SEQ ID NO: 1.

8. The method of claim 1, wherein said polypeptide comprises a sequence having at least 85% sequence identity to SEQ ID NO: 13.

9. The method of claim 8, wherein said inhibitor comprises the sequence of SEQ ID NO: 13.

10. The method of claim 1, wherein said treatment improves one or more symptoms of said APS.

11. The method of claim 10, wherein said one or more symptoms is selected from the group consisting of a blood clot, deep vein thrombosis, stroke, thrombocytopenia, heart valve disease, livedo reticularis, headache, oscillopsia, and pregnancy-related complications.

12. The method of claim 11, wherein said pregnancy-related complications are selected from miscarriage, pre-eclampsia, placental infarctions, early delivery, stillbirth, and mental and development retardation in a newborn.

13. The method of claim 1, wherein said subject is a mammal.

14. The method of claim 13, wherein said mammal is a human.

15. The method of claim 1, wherein said polypeptide inhibits or reduces binding of said dimeric β2GPI/antibody complex to cardiolipin.

16. The method of claim 1, wherein said polypeptide is administered 1 to 10 times per day, week, or month.

17. The method of claim 1, wherein said polypeptide is administered at a dosage of 0.01 to 2000 mg/kg.

18. The method of claim 1, wherein the amino acid sequence of said first LA module is different from the amino acid sequence of said second LA module.

19. The method of claim 1, wherein said first A1 domain comprises an amino acid sequence with 90% or more sequence identity to the amino acid sequence of SEQ ID NO: 2, 3, 14, or 15, and said second A1 domain comprises an amino acid sequence with 90% or more sequence identity to the amino acid sequence of SEQ ID NO: 2, 3, 14, or 15.

20. The method of claim 19, wherein said first A1 domain comprises an amino acid sequence with 90% or more sequence identity to the amino acid sequence of SEQ ID NO: 2 or 14 and said second A1 domain comprises an amino acid sequence with 90% or more sequence identity to the amino acid sequence of SEQ ID NO: 3 or 15.

21. The method of claim 1, wherein said first A1 domain comprises an amino acid sequence with 95% or more sequence identity to the amino acid sequence of SEQ ID NO: 2, 3, 14, or 15, and said second A1 domain comprises an amino acid sequence with 95% or more sequence identity to the amino acid sequence of SEQ ID NO: 2, 3, 14, or 15.

22. The method of claim 21, wherein said first A1 domain comprises an amino acid sequence with 95% or more sequence identity to the amino acid sequence of SEQ ID NO: 2 or 14 and said second A1 domain comprises an amino acid sequence with 95% or more sequence identity to the amino acid sequence of SEQ ID NO: 3 or 15.

23. The method of claim 1, wherein said first A1 domain comprises an amino acid sequence with 100% sequence identity to the amino acid sequence of SEQ ID NO: 2, 3, 14, or 15, and said second A1 domain comprises an amino acid sequence with 100% sequence identity to the amino acid sequence of SEQ ID NO: 2, 3, 14, or 15.

24. The method of claim 23, wherein said first A1 domain comprises an amino acid sequence with 100% sequence identity to the amino acid sequence of SEQ ID NO: 2 or 14 and said second A1 domain comprises an amino acid sequence with 100% sequence identity to the amino acid sequence of SEQ ID NO: 3 or 15.

25. A method of treating antiphospholipid syndrome in a subject in need thereof comprising administering a composition comprising a polypeptide,
 wherein said polypeptide comprises a first A1 domain of apolipoprotein E receptor 2 (ApoER2), wherein said A1 domain is the first low density lipoprotein (LDL) receptor-type A (LA) module of said ApoER2, a second A1 domain of said ApoER2, and a linker that joins said first A1 domain to said second A1 domain.

26. The method of claim 25, wherein said subject is a human.

\* \* \* \* \*

SEQUENCE LISTING

```
<160> NUMBER OF SEQ ID NOS: 15

<210> SEQ ID NO 1
<211> LENGTH: 78
<212> TYPE: PRT
<213> ORGANISM: Artificial Sequence
<220> FEATURE:
<223> OTHER INFORMATION: Synthetic Construct

<400> SEQUENCE: 1

Ala Glu Cys Glu Glu Asp Gln Phe Arg Cys Arg Asn Glu Arg Cys Ile
1               5                   10                  15

Pro Leu Val Trp Arg Cys Asp Glu Asp Asn Asp Cys Ser Asp Asn Ser
            20                  25                  30

Asp Glu Asp Asp Cys Gly Ser Ser Gly Cys Glu Glu Asp Gln Phe Arg
        35                  40                  45
```

```
Cys Arg Asn Glu Arg Cys Ile Pro Leu Val Trp Arg Cys Asp Glu Asp
    50                  55                  60

Asn Asp Cys Ser Asp Asn Ser Asp Glu Asp Cys Glu Ala
65                  70                  75

<210> SEQ ID NO 2
<211> LENGTH: 37
<212> TYPE: PRT
<213> ORGANISM: Artificial Sequence
<220> FEATURE:
<223> OTHER INFORMATION: Synthetic Construct

<400> SEQUENCE: 2

Ala Glu Cys Glu Glu Asp Gln Phe Arg Cys Arg Asn Glu Arg Cys Ile
1               5                   10                  15

Pro Leu Val Trp Arg Cys Asp Glu Asp Asn Asp Cys Ser Asp Asn Ser
            20                  25                  30

Asp Glu Asp Asp Cys
        35

<210> SEQ ID NO 3
<211> LENGTH: 37
<212> TYPE: PRT
<213> ORGANISM: Artificial Sequence
<220> FEATURE:
<223> OTHER INFORMATION: Synthetic Construct

<400> SEQUENCE: 3

Cys Glu Glu Asp Gln Phe Arg Cys Arg Asn Glu Arg Cys Ile Pro Leu
1               5                   10                  15

Val Trp Arg Cys Asp Glu Asp Asn Asp Cys Ser Asp Asn Ser Asp Glu
            20                  25                  30

Asp Asp Cys Glu Ala
        35

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Gly Ser Ser Gly
1

<210> SEQ ID NO 5
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (1)..(1)
<223> OTHER INFORMATION: May be repeated 0 to 9 times

<400> SEQUENCE: 5

Gly
1

<210> SEQ ID NO 6
<211> LENGTH: 1
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: REPEAT
<222> LOCATION: (1)..(1)
<223> OTHER INFORMATION: May be repeated 0 to 9 times

<400> SEQUENCE: 6

Ser
1

<210> SEQ ID NO 7
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (1)..(1)
<223> OTHER INFORMATION: May be repeated 0 to 9 times

<400> SEQUENCE: 7

Ala
1

<210> SEQ ID NO 8
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (1)..(2)
<223> OTHER INFORMATION: May be repeated 0 to 9 times

<400> SEQUENCE: 8

Gly Ser
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (1)..(4)
<223> OTHER INFORMATION: May be repeated 0 to 9 times

<400> SEQUENCE: 9

Gly Ser Ser Gly
1

<210> SEQ ID NO 10
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (1)..(3)
<223> OTHER INFORMATION: May be repeated 0 to 9 times

<400> SEQUENCE: 10

Gly Ser Gly
1
```

```
<210> SEQ ID NO 11
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (1)..(3)
<223> OTHER INFORMATION: May be repeated 0 to 9 times

<400> SEQUENCE: 11

Gly Ser Ser
1

<210> SEQ ID NO 12
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (1)..(2)
<223> OTHER INFORMATION: May be repeated 0 to 9 times

<400> SEQUENCE: 12

Gly Ala
1

<210> SEQ ID NO 13
<211> LENGTH: 61
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (30)..(32)
<223> OTHER INFORMATION: May be repeated 0 to 9 times

<400> SEQUENCE: 13

Ala Cys Arg Asn Glu Arg Ser Ile Pro Leu Val Trp Arg Cys Asp Glu
1               5                   10                  15

Asp Asn Asp Cys Ser Asp Asn Ser Asp Glu Asp Asp Cys Gly Ser Gly
            20                  25                  30

Cys Arg Asn Glu Arg Ser Ile Pro Leu Val Trp Arg Cys Asp Glu Asp
        35                  40                  45

Asn Asp Cys Ser Asp Asn Ser Asp Glu Asp Asp Cys Ala
    50                  55                  60

<210> SEQ ID NO 14
<211> LENGTH: 29
<212> TYPE: PRT
<213> ORGANISM: Artificial Sequence
<220> FEATURE:
<223> OTHER INFORMATION: Synthetic Construct

<400> SEQUENCE: 14

Ala Cys Arg Asn Glu Arg Ser Ile Pro Leu Val Trp Arg Cys Asp Glu
1               5                   10                  15

Asp Asn Asp Cys Ser Asp Asn Ser Asp Glu Asp Asp Cys
            20                  25

<210> SEQ ID NO 15
```

```
<211> LENGTH: 29
<212> TYPE: PRT
<213> ORGANISM: Artificial Sequence
<220> FEATURE:
<223> OTHER INFORMATION: Synthetic Construct

<400> SEQUENCE: 15

Cys Arg Asn Glu Arg Ser Ile Pro Leu Val Trp Arg Cys Asp Glu Asp
1               5                   10                  15

Asn Asp Cys Ser Asp Asn Ser Asp Glu Asp Asp Cys Ala
            20                  25
```